(12) United States Patent
Srinivasa et al.

(10) Patent No.: US 11,289,175 B1
(45) Date of Patent: Mar. 29, 2022

(54) METHOD OF MODELING FUNCTIONS OF ORIENTATION AND ADAPTATION ON VISUAL CORTEX

(71) Applicant: HRL LABORATORIES LLC, Malibu, CA (US)

(72) Inventors: Narayan Srinivasa, Oak Park, CA (US); Qin Jiang, Park Oaks, CA (US)

(73) Assignee: HRL Laboratories, LLC, Malibu, CA (US)

( * ) Notice: Subject to any disclaimer, the term of this patent is extended or adjusted under 35 U.S.C. 154(b) by 0 days.

(21) Appl. No.: 13/691,130

(22) Filed: Nov. 30, 2012

(51) Int. Cl.
*G16B 5/00* (2019.01)
(52) U.S. Cl.
CPC .................... *G16B 5/00* (2019.02)
(58) Field of Classification Search
CPC ............... G05B 13/024; G05B 13/027; G06F 17/30247; G06K 9/6252; G06N 3/04; G06N 3/06; G06N 3/08; G06N 3/088; G16B 5/00
See application file for complete search history.

(56) References Cited

U.S. PATENT DOCUMENTS

| | | | | |
|---|---|---|---|---|
| 2003/0228054 | A1* | 12/2003 | Deco | G06K 9/4623 382/156 |
| 2012/0330870 | A1* | 12/2012 | Aparin | 706/19 |
| 2013/0339280 | A1* | 12/2013 | Hunzinger | G06N 3/08 706/25 |

OTHER PUBLICATIONS

Over Choe et al. "Self-organization and segmentation in a laterally connected orientation map of spiking neurons", Neurocomputing 21 (1998), pp. 139-157.*
Miikkulainen et al. "A Self-Organizing Neural Network Model of Theprimary Visual Cortex", ICONIP, 1998, pp. 4.*
Olson et al. "A Neural Network Model for the Development of Simple and Complex Cell Receptive Fields Within Cortical Maps of Orientation and Ocular Dominance", Technical Report CAS/CNS-96-021, 1997, pp. 43.*
Neural coding, https://en.wikipedia.org/wiki/Neural_coding, Jan. 24, 2012, pp. 6.*
Bonhoeffer, Tobias et al., "Iso-orientation domains in cat visual cortex are arranged in pinwheel-like patterns," Letters to Nature, vol. 353, Oct. 3, 1991, Nature Publishing Group, pp. 429-431.
Bartsch, A.P. et al., "Combined Hebbian development of geniculocortical and lateral connectivity in a model of primary visual cortex," Biological Cybernetics 84, 2001, Springer-Verlag, pp. 41-55.

* cited by examiner

*Primary Examiner* — Li Wu Chang
(74) *Attorney, Agent, or Firm* — Lewis Roca Rothgerber Christie, LLP

(57) ABSTRACT

A method is disclosed. The method models a plurality of visual cortex neurons, models one or more connections between at least two visual cortex neurons in the plurality of visual cortex neurons, assigns synaptic weight value to at least one of the one or more connections, simulates application of one or more electrical signals to at least one visual cortex neuron in the plurality of visual cortex neurons, adjusts the synaptic weight value assigned to at least one of the one or more connection based on the one or more electrical signals, and generates an orientation map of the plurality of visual cortex neurons based on the adjusted synaptic weight values.

19 Claims, 15 Drawing Sheets

METHOD OF MODELING FUNCTIONS OF ORIENTATION AND ADAPTATION ON VISUAL CORTEX

STATEMENT REGARDING FEDERALLY SPONSORED RESEARCH OR DEVELOPMENT

The present invention was made with support from the United States Government under Grant number HR0011-09-C-0001 (SyNAPSE) awarded by the Defense Advanced Research Project Agency (DARPA). The United States Government has certain rights in the invention.

FIELD

The present invention relates to simulating neural networks of human biological systems.

BACKGROUND

Computational models for simulating neural networks of human biological systems may be an important tool for studying human biological systems and developing advanced bio-inspired artificial intelligent systems. For example, the computational models for simulating neural networks of human biological systems may be used to improve the capability of computer vision such as automation in manufacture, vision based safety system and/or robotics.

An exemplary computing model to simulate human visual orientation formation process is described in an article by A. P. Bartsch and J. L. van Hemmen, "Combined Hebbian development of geniculocortical and lateral connectivity in a model of primary visual cortex," *Biological Cybernetics*, Springer-Verlag, no. 84, pp. 41-55, 2001, which is incorporated herein by reference in its entirety. Although this article describes simulating 32×32 neurons, it is doubtful that any known hardware is sufficient to simulate millions of neurons due to the complexity of the learning model proposed in the article.

Contrary to the prior art, a presently disclosed system may be used to simulate millions of neurons, which is more close to the actual biological structures of human visual cortex.

SUMMARY

According to a first aspect of the present disclosure, a method is disclosed, the method comprising: modeling a plurality of visual cortex neurons; modeling one or more connections between at least two visual cortex neurons in the plurality of visual cortex neurons; assigning synaptic weight value to at least one of the one or more connections; simulating application of one or more electrical signals to at least one visual cortex neuron in the plurality of visual cortex neurons; adjusting the synaptic weight value assigned to at least one of the one or more connection based on the one or more electrical signals; and generating an orientation map of the plurality of visual cortex neurons based on the adjusted synaptic weight values.

According to a second aspect of the present disclosure, a computer system is disclosed, the computer system comprising: a memory to store computer-readable code; and a processor operatively coupled to said memory and configured to implement said computer-readable code, said computer-readable code configured to: model a plurality of visual cortex neurons; model one or more connections between at least two visual cortex neurons in the plurality of visual cortex neurons; assign synaptic weight value to at least one of the one or more connections; simulate application of one or more electrical signals to at least one visual cortex neuron in the plurality of visual cortex neurons; adjust the synaptic weight value assigned to at least one of the one or more connection based on the one or more electrical signals; and generate an orientation map of the plurality of visual cortex neurons based on the adjusted synaptic weight values.

According to a third aspect of the present disclosure, a system is disclosed, the system comprising: means for modeling a plurality of visual cortex neurons; means for modeling one or more connections between at least two visual cortex neurons in the plurality of visual cortex neurons; means for assigning synaptic weight value to at least one of the one or more connections; means for simulating application of one or more electrical signals to at least one visual cortex neuron in the plurality of visual cortex neurons; means for adjusting the synaptic weight value assigned to at least one of the one or more connection based on the one or more electrical signals; and means for generating an orientation map of the plurality of visual cortex neurons based on the adjusted synaptic weight values.

Figure 1A:
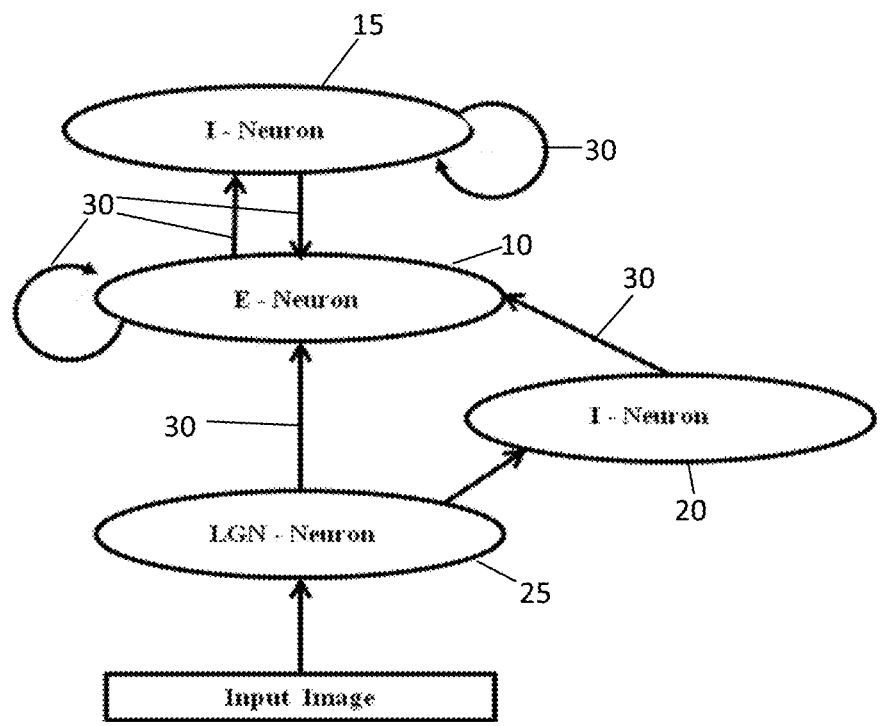
FIG. 1a depicts neuron layers in accordance with some embodiments.

In the following description, like reference numbers are used to identify like elements. Furthermore, the drawings are intended to illustrate major features of exemplary embodiments in a diagrammatic manner. The drawings are not intended to depict every feature of every implementation nor relative dimensions of the depicted elements, and are not drawn to scale.

DETAILED DESCRIPTION

In the following description, numerous specific details are set forth to clearly describe various specific embodiments disclosed herein. One skilled in the art, however, will understand that the presently claimed invention may be practiced without all of the specific details discussed below.

In other instances, well known features have not been described so as not to obscure the invention.

Human visual system is potentially one of the most advanced perception systems in nature. Although biological structures and neuron properties of human visual system are well known, it is not well understood how the high level visual functions are formed in human visual cortex. One possible way to help understand the formation of the high level visual functions is to simulate visual cortex from neuron level in large-scale (millions of neurons). Therefore, finding computational neural models for human visual system may provide a better understanding of human visual system in neuroscience and improve computer vision technology.

In recent years, many neural models for human visual system have been proposed in the literature. Although the existing, prior art, models can only simulate visual neuron-network in small-scale, high-level visual functions require simulating the behaviors of neuron populations which involve thousands or millions of neurons. In order to study high-level visual functions of human visual cortex, a need exists to be able to simulate neural networks at the scale of neuron populations (i.e. millions of neurons). The idea is to construct visual cortex from neuron level; when the neural network reaches the size of neuron populations, it may be possible to observe the high level visual functions from the neural network. In order to deal with a simulation with thousands or millions of neurons, it may be required that computational neuron models be hardware implementable.

In the present disclosure, a computational model/structure for simulating human visual cortex, for simulating visual orientation formation and visual adaptation to light conditions, is disclosed. Simulation results, presently described, show that presently described computational structure can achieve high-level visual behaviors: orientation formation and adaptation to lighting condition changes. The presently disclosed model may be fully hardware implementable, which makes it possible to construct a neural network that is comparable to biological human visual cortex in terms of neuron numbers.

The presently disclosed system may be used in applications such as, for example, automation in manufacture, vision based safety system, robotics, satellite based imaging systems, and/or computer vision.

In an exemplary embodiment, the presently disclosed system/computation model/structure may use four layers (one excitatory neuron layer 10, two inhibitory neuron layers 15, 20 and one lateral geniculate nucleus (LGN) neuron layer 25 which are interconnected by synaptic connections 30) as shown in FIG. 1a of neural networks to model primary visual cortex.

Figure 1B:
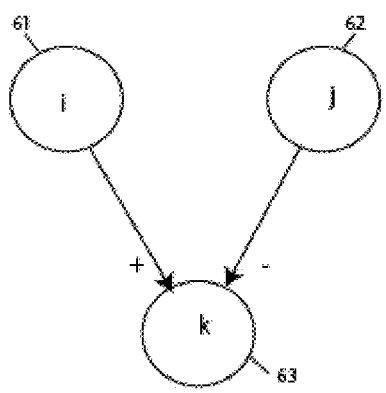
FIG. 1b depicts neurons in accordance with some embodiments.

Referring to FIG. 1b, excitatory neuron 61 and inhibitory 62 are depicted releasing electrical spiking to a neuron 63. The membrane potential of the neuron 63 may be described with Equations (1), (2) and (3)

$$u_k(t) = \varepsilon_{ik}(t) + \varepsilon_{ik}(t) \tag{1}$$

$$\varepsilon_{ik}(t) = u_0 \left[ 1.0 - \exp\left(\frac{-(t - t_f)}{\tau_{ik}}\right) \right] \tag{2}$$

$$\text{and } \varepsilon_{jk}(t) = u_0 \left[ \exp\left(\frac{-(t - t_f)}{\tau_{jk}}\right) - 1.0 \right] \tag{3}$$

The variables, $\tau_{ik}$ and $\tau_{jk}$, are membrane constants; the variable $t^f$ is neuron firing time. The component $\varepsilon_{ik}(t)$ is the contribution from the neuron 61 while the component $\varepsilon_{jk}(t)$ is the contribution from the neuron 62. For $t \geq t^f$, $\varepsilon_{ik}(t) \geq 0.0$ and $\varepsilon_{jk}(t) \leq 0.0$.

Referring to FIG. 1a, in a neuron network, every neuron receives synaptic signals from other neurons through synaptic connections 30 and transmits synaptic signals to other neurons through synaptic connections 30. In an exemplary embodiment, a leaky integrate-and-fire model may be implemented to simulate the dynamics of single neuron. The leaky integrate-and-fire model is described by the following Equation (4):

$$\tau_m \frac{du(t)}{dt} = -u(t) + RI(t) \tag{4}$$

The variable u(t) is the membrane potential; the variable I(t) is the membrane current; and the constants, $\tau_m$ and R, are the membrane time constant and resistance of the neuron, respectively. When the membrane potential of a neuron crosses a threshold value, the neuron releases a spiking signal (neuron firing) to other neurons. In terms of action on other neurons, a neuron is broadly classified as an inhibitory neuron or an excitatory neuron. An inhibitory neuron releases inhibitory synaptic signals, which cause a decrease in neuron firing on its target neurons while an excitatory neuron releases excitatory synaptic signals, which cause an increase in neuron firing on its target neurons. The lateral geniculate nucleus (LGN) neuron refers to a biological region of neurons. The LGN plays a bridge role that link between the retinal of an eye and a visual cortex. That is, LGN neurons receive biological signals (spiking) from the retinal of the eye and transmit these biological signals to the visual cortex. In one exemplary embodiment according to the present disclosure LGN neurons are simulates as excitatory neurons.

Figure 2:
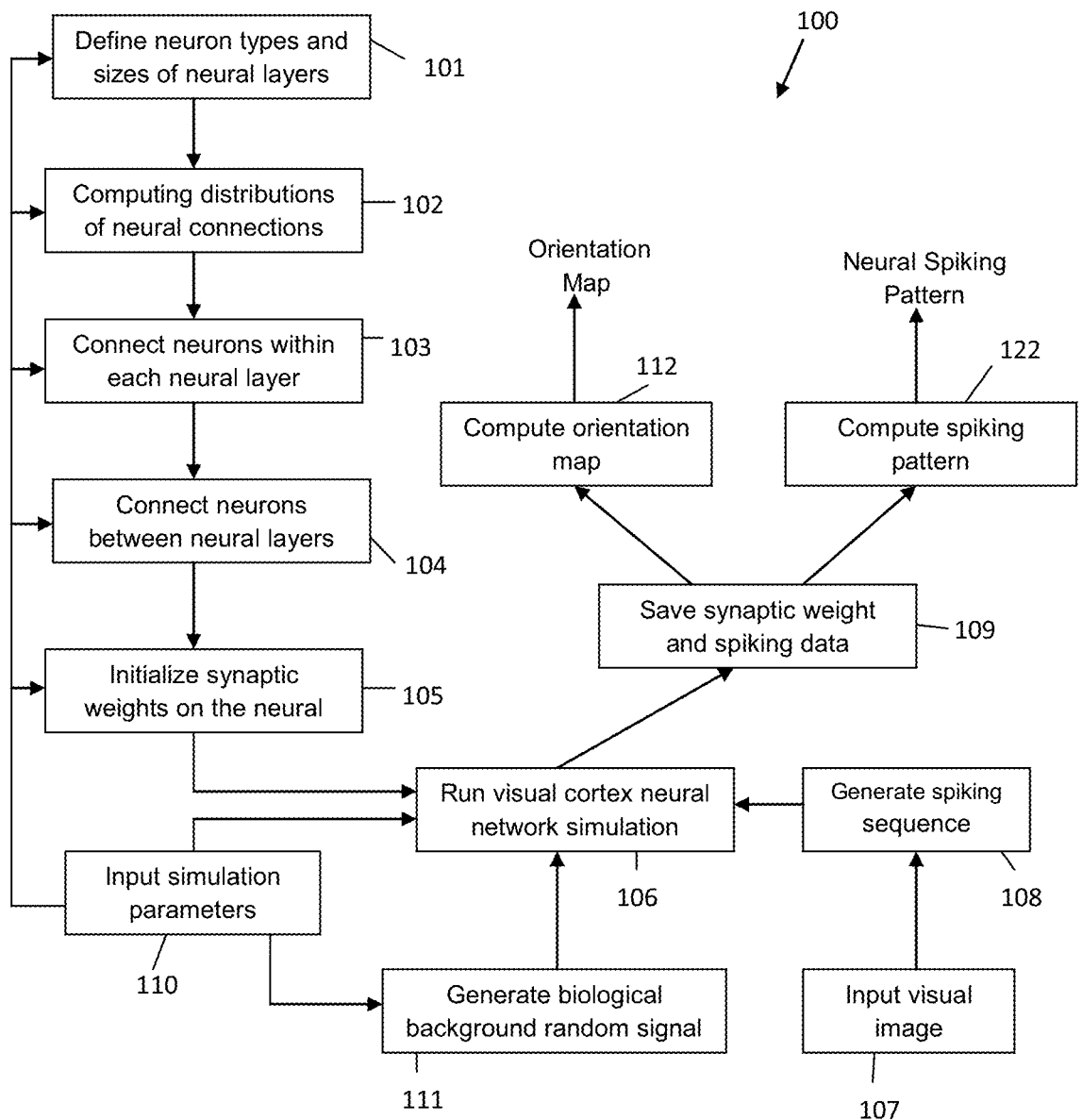
FIG. 2 depicts a flow chart of a computational model in accordance with some embodiments.

In an exemplary embodiment, a computational model 100 according to the present disclosure may be implemented as shown in FIG. 2. The computational model 100 may comprise a defining stage 101 configured to allow one or more users to define neuron types and/or define sizes of neural layers 10, 15, 20 and/or 25. In an exemplary embodiment, the one or more users may define one or more neurons as excitatory neuron, inhibitory neuron and/or lateral geniculate nucleus neuron. In another exemplary embodiment, the defining stage 101 may arrange the neurons into matrices. For example, the neurons may be arranges into a matrix that is 128×128 or any other predetermined dimensions. In an exemplary embodiment, the one or more users may define the size of the matrix for the neurons.

In another exemplary embodiment, the computational model 100 may comprise parameter stage 110 configured to allow the one or more users to interact with the computational model 100 and provide parameters/input.

In another exemplary embodiment, the computational model 100 may also comprise a computation stage 102 configured to compute connections between every neuron defined within stage 101 with a plurality of other neurons associated with an adjacent neuron layer or a plurality of other neurons associated with the same neuron layer.

Figure 4:
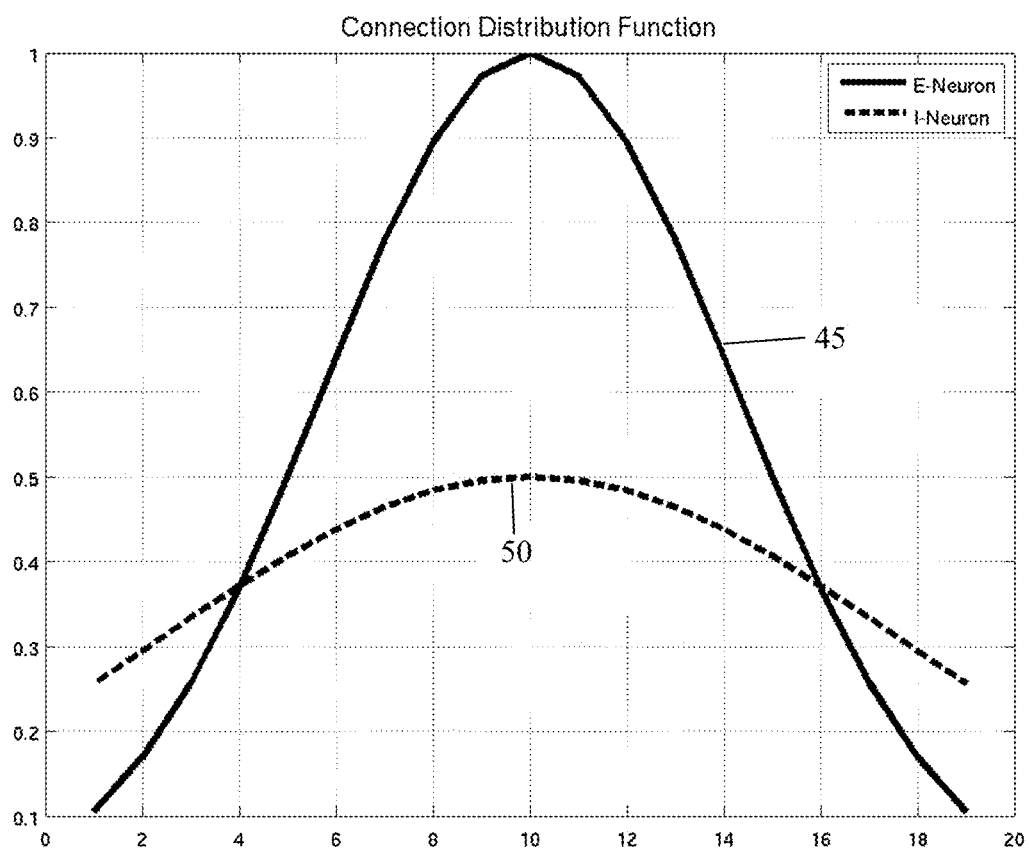
FIG. 4 depicts graphs in accordance with some embodiments.

In an exemplary embodiment, the neural connection stage 102 may implement a Gaussian density functions to model the random connectivity between neurons. The excitatory neurons and inhibitory neurons may use different Gaussian density functions to model the connectivity between neurons because the excitatory neurons have a more concentrated connectivity, while the inhibitory neurons have a wider and flatter connectivity. Referring to FIG. 4, graph 45 represents an exemplary, one dimensional, Gaussian density function for determining connectivity of an excitatory neuron to a plurality of adjacent excitatory neurons and graph 50 represents an exemplary, one dimensional, Gaussian density function for determining connectivity of an inhibitory neuron to a plurality of adjacent inhibitory neurons. As described above and shown in graphs 45 and 50, the excitatory neurons and inhibitory neurons may use different Gaussian density functions.

Mathematically, excitatory neurons' connection probability may be represented by Equation (5) below and inhibitory neurons' connection probability may be represented by Equation (6) below:

$$P_E(x, y) = 1.5 * e^{\frac{-[(x-x_0)^2+(y-y_0)^2]}{2*\sigma_e}} \quad (5)$$

$$P_I(x, y) = 3.5 * e^{\frac{-[(x-x_0)^2+(y-y_0)^2]}{2*\sigma_i}} \quad (6)$$

Figure 5A:
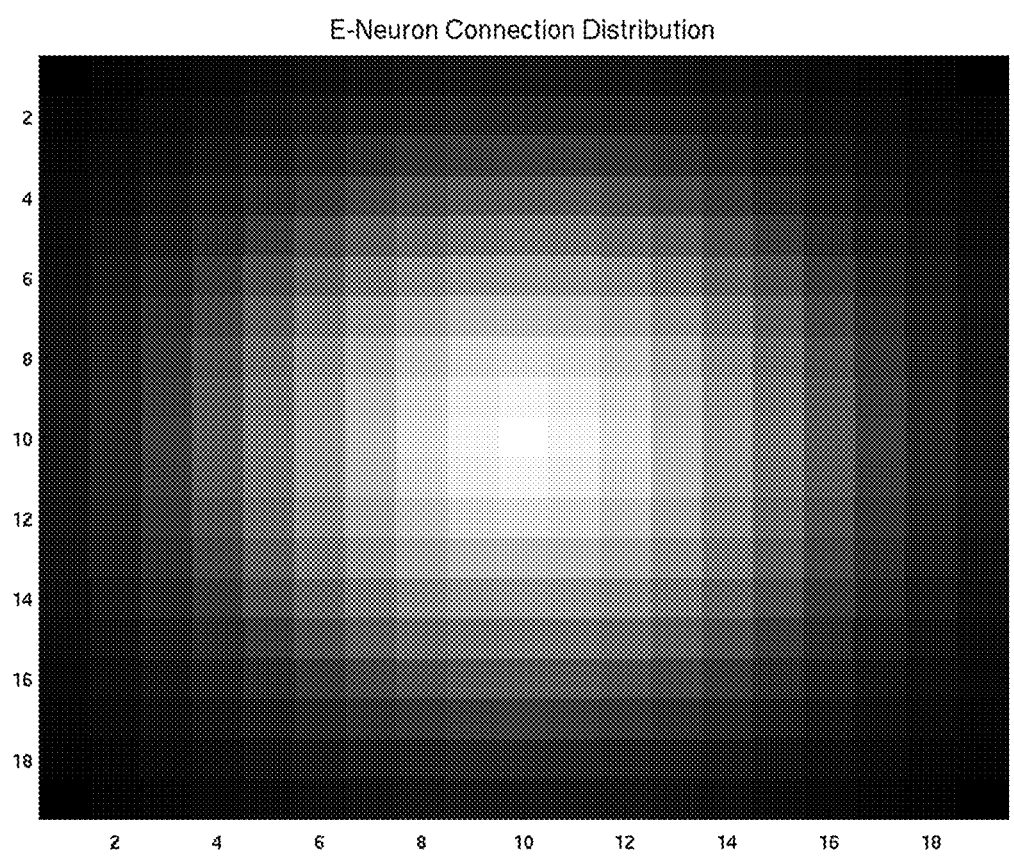
FIGS. 5a-c depict connection distributions in accordance with some embodiments.
Figure 5B:
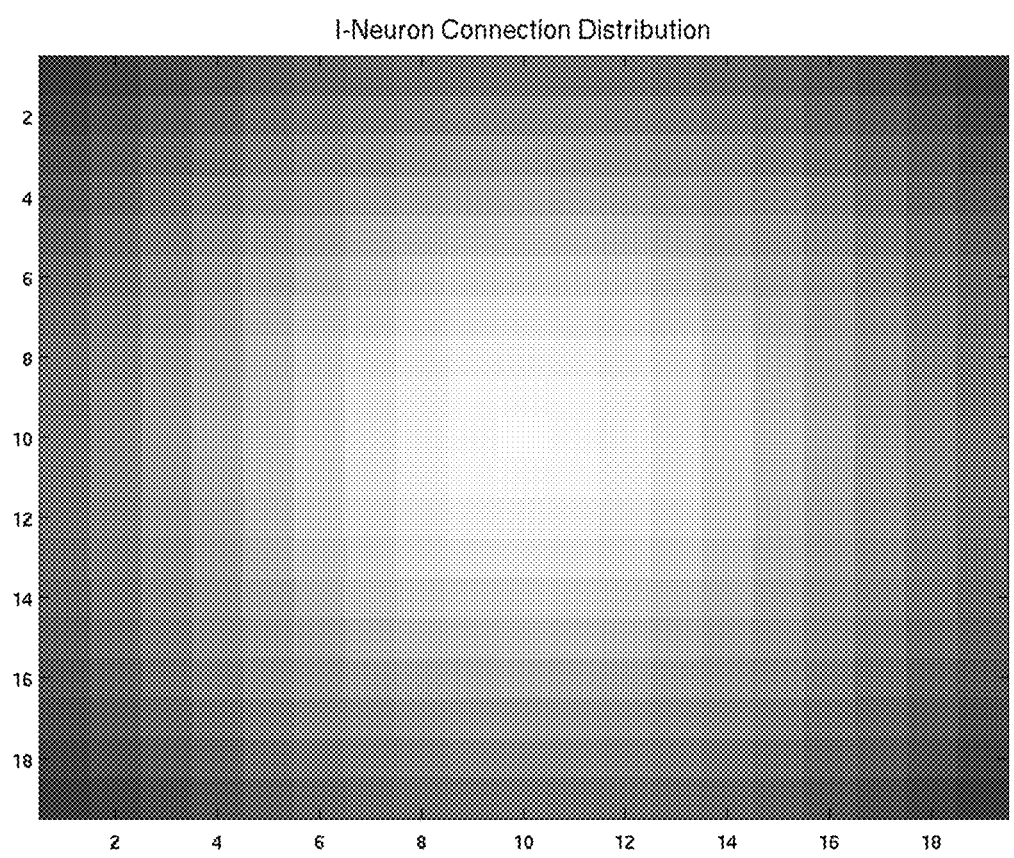
Figure 5C:
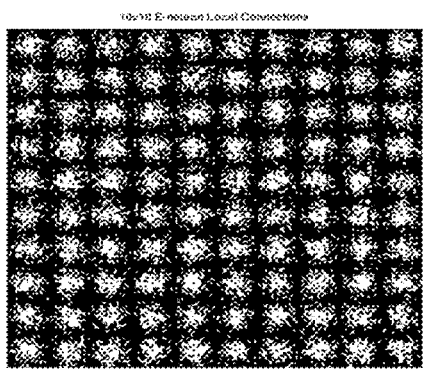

The point, $(x_0, y_0)$, is the position of the center neuron. FIGS. 5a-b represent a simulation with the connectivity neighborhood of 19×19. FIG. 5a depicts excitatory neuron connection distribution and FIG. 5b depicts inhibitory neuron connection distribution. In another embodiment, the local neuron connections of 10×10 neurons are depicted in FIG. 5c. As shown in FIG. 5c, host neurons are located at the centers of the clusters. In each cluster, a white point indicates a connection from the host neuron to one of its neighboring neurons. Most of neuron connections are Gaussian-distributed around the center neurons, which show the connectivity decreases as the distance from a center neuron increases.

In FIGS. 5a-b, bright region represents high connection probability, while dark region represents low connection probability. As shown in FIGS. 5a-b, as the distance increases (far away from the center neuron), the neuron connection probability decreases. As a result, a dense neuron connection is generated around the center and a sparse neuron connection is generated near the boundaries of the connection neighborhood.

In another exemplary embodiment, the neural connection stage 102 may implement a Uniform distribution function and/or Random distribution function to compute connections between every neuron defined within stage 101 with a plurality of other neurons associated with an adjacent neuron layer or a plurality of other neurons associated with the same neuron layer.

Figure 3:
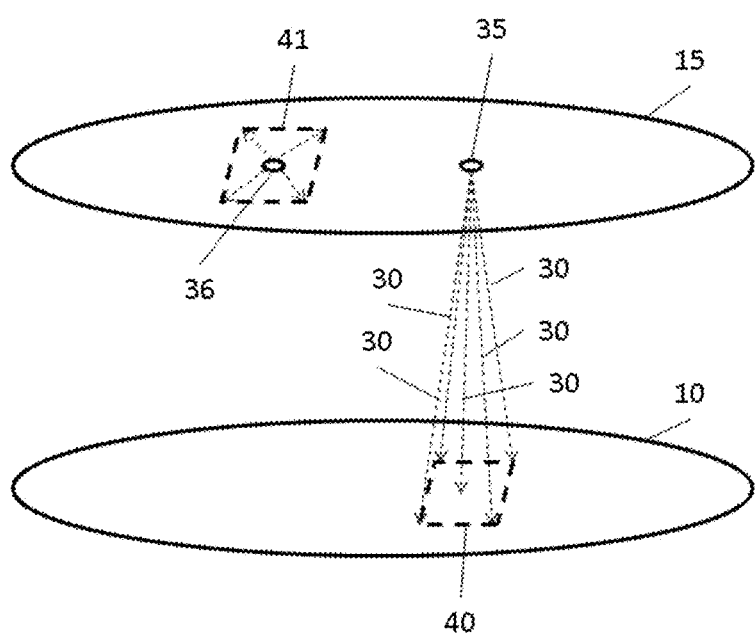
FIG. 3 depicts neuron connections in accordance with some embodiments.

In another exemplary embodiment, the computational model 100 may also comprise a neural connection stage 103 configured to connect every neuron defined within stage 101 with a plurality of other neurons associated with the same neuron layer based on computations from stage 102. FIG. 3 depicts an example of an inhibitory neuron 36 of the neuron layer 15 connected to a plurality of inhibitory neurons associated with a region/connectivity neighborhood 41 of the same neuron layer 15. The inhibitory neuron 36 may be randomly connected to the plurality of inhibitory neurons within the connectivity neighborhood 41.

In another exemplary embodiment, the computational model 100 may also comprise a neural connection stage 104 configured to connect every neuron defined within stage 101 with a plurality of other neurons associated with an adjacent neuron layer based on computations from stage 102. FIG. 3 depicts an example of an inhibitory neuron 35 of the neuron layer 15 connected to a plurality of excitatory neurons associated with a region/connectivity neighborhood 40 of the adjacent neuron layer 10. The inhibitory neuron 35 may be randomly connected to the plurality of excitatory neurons within the connectivity neighborhood 40.

In another exemplary embodiment, the computational model 100 may also comprise a synaptic weight stage 105 configured to assign initial synaptic weight values to each neuron's connection to other neurons. The synaptic weight values for each connection establish the strength of that connection. The higher the synaptic weight values, the stronger the connection. In one exemplary embodiment, the synaptic weight values may be assigned randomly.

In another exemplary embodiment, the computational model 100 may also comprise a simulation stage 106 configured to randomly trigger one or more neurons by simulating application of one or more random electrical signals. In an exemplary embodiment, the simulation stage 106 may trigger one or more neurons by simulating application of millions of electrical signals as specified by the one or more users. As the simulation stage 106 applies electrical signals, a spike timing-dependent plasticity (STDP) learning may be applied to adjust the synaptic weight values assigned to each connection.

In an exemplary embodiment of the simulation stage 106, the synaptic weights in the neural network may be learned by spike timing-dependent plasticity (STDP). One advantage of using STDP learning is that it is computationally efficient and hardware implementable. In STDP learning, if $t_{pre}$ and $t_{post}$ are the spiking times for a pre-synaptic spike and a post-synaptic spike, the corresponding synaptic conductance may be computed with Equations (7) to (9) below:

$$g_{new} = g_{old} + \Delta g \quad (7)$$

and $$\Delta g = g_{max} * F(\Delta t) \quad (8)$$

with $$F(\Delta t) = \begin{cases} A_+ * \exp\left(\frac{\Delta t}{\tau_+}\right), \text{ if } \Delta t < 0 \\ -A_- * \exp\left(\frac{\Delta t}{\tau_-}\right), \text{ if } \Delta t \geq 0 \end{cases} \quad (9)$$

Where $\Delta t = t_{pre} - t_{post}$. The constants, $A_+$ and $A_-$, determine the maximum amount of synaptic modification. The time constants, $\tau_+$ and $\tau_-$, determine the ranges of pre- to post-synaptic spike intervals.

In an exemplary embodiment, the computational model 100 may also comprise a random signal stage 111 configured to obtain input/parameters from the one or more users through the parameter stage 110 and generate random signals based on the obtained input/parameters for the simulation stage 106. In this embodiment, the simulation stage 106 may randomly trigger one or more neurons based on the random signals generated by the random signal stage 111.

Figure 6A:
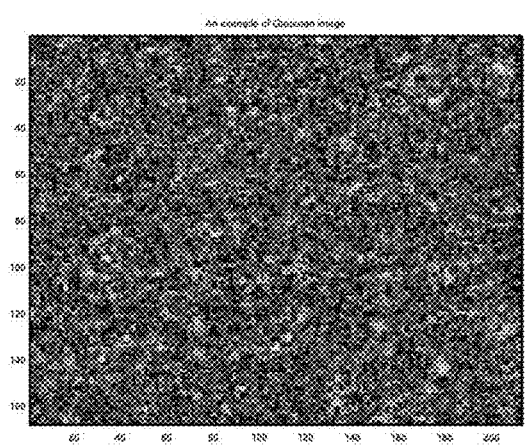
FIG. 6a depicts input visual image in accordance with some embodiments.
Figure 6B:
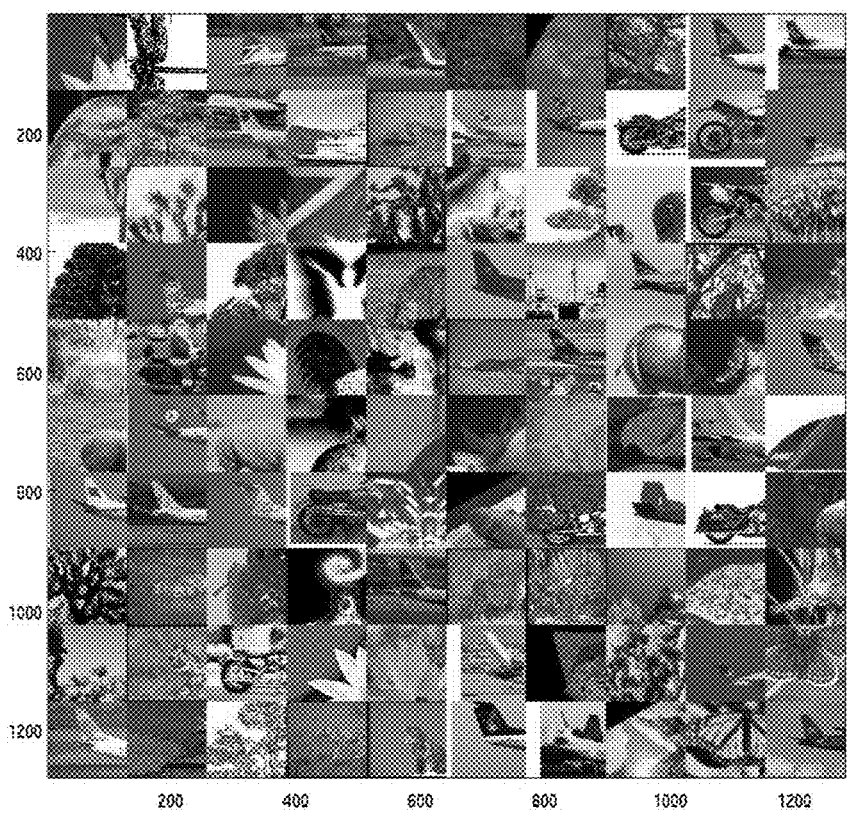
FIG. 6b depicts another input visual image in accordance with some embodiments.

In another exemplary embodiment, the computational model 100 may also comprise an input stage 107 configured to provide one or more input visual images. In an exemplary embodiment, at least one of the one or more visual images may be Gaussian random field image as shown in FIG. 6a. In an exemplary embodiment, the one or more visual images may be random images as shown in FIG. 6b.

In another exemplary embodiment, the computational model 100 may also comprise a spiking stage 108 configured to generate a spiking sequence of electrical signals based on the image provided by the input stage 107. In an exemplary embodiment, for every pixel of the input visual image, the model 108 may compute a mean value of Poisson distribution from the intensity value of the pixel and a given range of firing rate; and then, a spiking interval may be calculated from the mean value and the Poisson distribution. The spiking interval may be used to generate the next spike, an impulse at a specific time point. In an exemplary embodiment, the spiking sequence of the electrical signals generated by the spiking stage 108 may be applied to the simulation stage 106 to further trigger the one or more neurons. As the simulation stage 106 applies the spiking sequence of the electrical signals, the STDP learning may further be applied to adjust the synaptic weight values assigned to each neural connection.

In another exemplary embodiment, the computational model 100 may also comprise a retaining stage 109 configured to store/save the adjusted synaptic weight values associated with each neural connection and to store/save the spiking sequence generated by every neuron defined at the defining stage 101.

In another exemplary embodiment, the computational model 100 may also comprise a spike computation stage 122 configured to compute statistical patterns of spiking activities generated by saved spiking sequences at the retaining stage 109. Spiking patterns may be used to monitor/analyze the behaviors of the neural networks.

In another exemplary embodiment, the computational model 100 may also comprise an orientation mapping stage 112 configured to generate orientation map based on the adjusted synaptic weight values stored by the retaining stage 109. An exemplary embodiment of the orientation mapping stage 112 is shown in FIG. 7.

Figure 7:
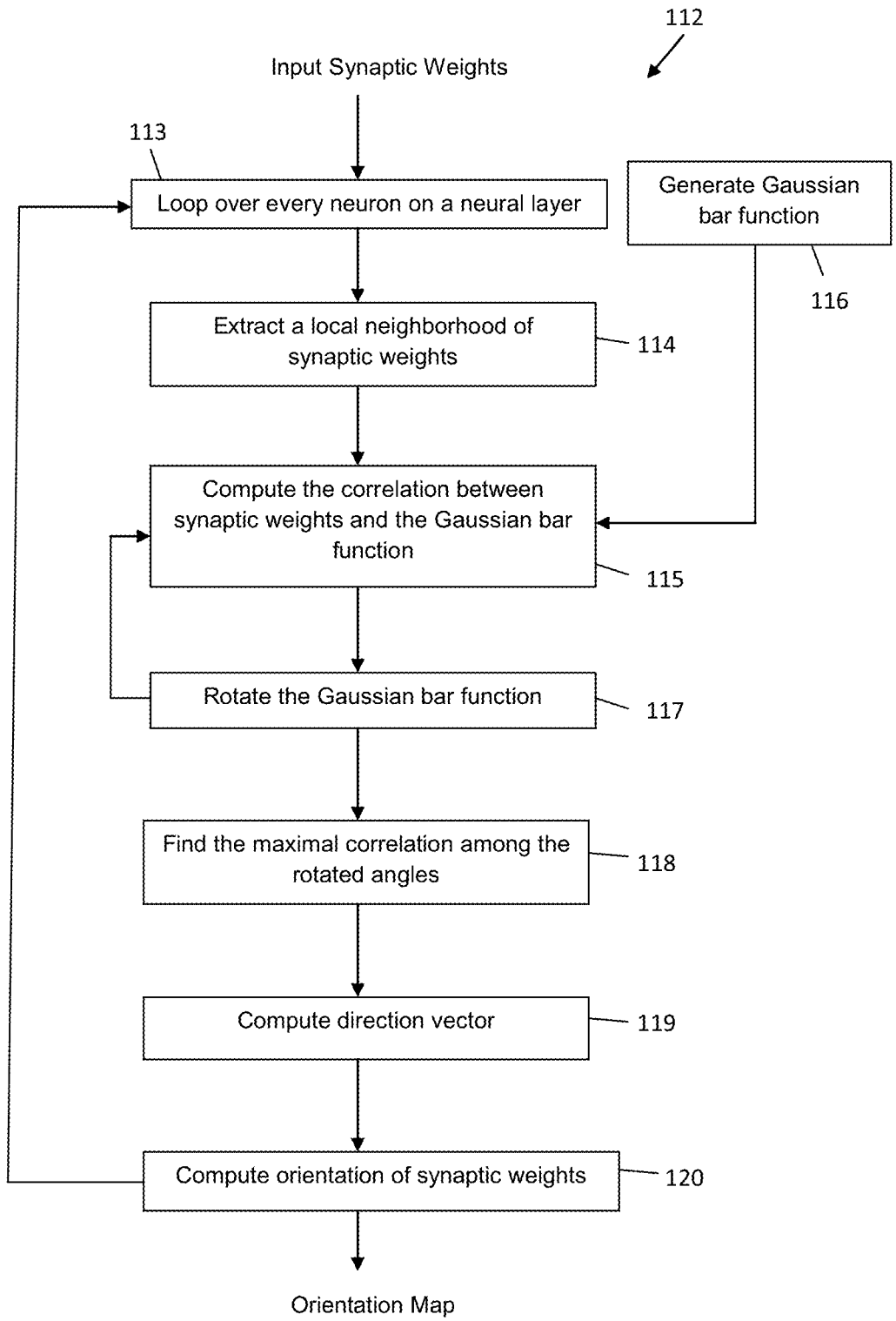
FIG. 7 depicts another flow chart of a computational model in accordance with some embodiments.

Referring to FIG. 7, in an exemplary embodiment, the orientation mapping stage 112 may comprise a looping stage 113 configured to analyze one excitatory neuron at a time and determine orientation sensitivity for each excitatory neuron based on the synaptic weight values stored in the retaining stage 109. In one embodiment, the looping stage 113 is configured to analyze one or more inhibitory neurons. In another embodiment, the looping stage 113 is configured to analyze one or more lateral geniculate nucleus (LGN) neurons.

In an exemplary embodiment, the orientation mapping stage 112 may also comprise an extraction stage 114 configured to associate a plurality of excitatory neurons with the excitatory neuron analyzed by the looping stage 113 and extract synaptic weight values for each excitatory neuron of the plurality of excitatory neurons. In an exemplary embodiment, the computational model 100 may be configured to allow one or more users to determine the number of excitatory neurons to be associated with each excitatory neuron analyzed by the looping stage 113. In an exemplary embodiment, the extracted synaptic weight values for each excitatory neuron of the plurality of excitatory neurons may be stored in a matrix. The matrix may be, for example, 19×19, 11×11 or any other predetermined value.

In an exemplary embodiment, the orientation mapping stage 112 may also comprise a computation stage 115 configured to compute correlation between the synaptic weight values extracted in stage 114 and, for example, a Gaussian distribution bar function 116.

In an exemplary embodiment, the orientation mapping stage 112 may also comprise a rotation stage 117 configured to rotate the Gaussian bar function 116 as an orientation template to search for the best orientation match within the synaptic weight values extracted in stage 114. If the center excitatory neuron is located at (0,0), the Gaussian bar function may be given by Equation (10) below:

$$G_{xy}(\phi, p) = \exp\left\{\frac{-[x\cos\phi + y\sin\phi - p]^2}{2^*\sigma_a^2}\right\}^* \quad (10)$$
$$\exp\left\{\frac{-[y\cos\phi + x\sin\phi]^2}{2^*\sigma_b^2}\right\} - G_0(\phi, p)$$

The x and y may take values within 19×19, 11×11 or any other predetermined range. The function $G_0(\phi, p)$ may be chosen so that $$\sum_{xy} G_{xy}(\phi, p) = 0.$$

For each of the four orientations, $\phi \in \{0°, 45°, 90°, 135°\}$, the orientation mapping stage 112 may also comprise a correlation stage 118 configured to vary parameter p to determine the maximal orientation match using Equation (11) below:

$$R(\phi) = \max_p\left[\sum_{xy} w(x, y)G_{xy}(\phi, p)\right] \quad (11)$$

In an exemplary embodiment, the orientation mapping stage 112 may also comprise a direction vector stage 119 configured to generate a direction vector. The direction vector may be constructed by $\vec{d}(\phi) = (R(\phi), 2\phi)$. Then, the four direction vectors may be summed using Equation (12) below:

$$\vec{S} = (R_s, \phi_s) = \vec{d}(0°) + \vec{d}(45°) + \vec{d}(90°) + \vec{d}(135°) \quad (12)$$

The orientation of synaptic weights may be determined in orientation stage 120 using Equation (13) below:

$$\phi_{or} = \phi_s/2 \quad (13)$$

In an exemplary embodiment, after completing orientation stage 120, the orientation mapping stage 112 may assign a color to the excitatory neuron based on the orientation value determined by the orientation stage 120.

In an exemplary embodiment, after completing orientation stage 120, the orientation mapping stage 112 may loop back to the looping stage 113 to analyze another excitatory neuron and determine orientation sensitivity for the next excitatory neuron based on the synaptic weight values stored in the retaining stage 109.

Figure 8A:
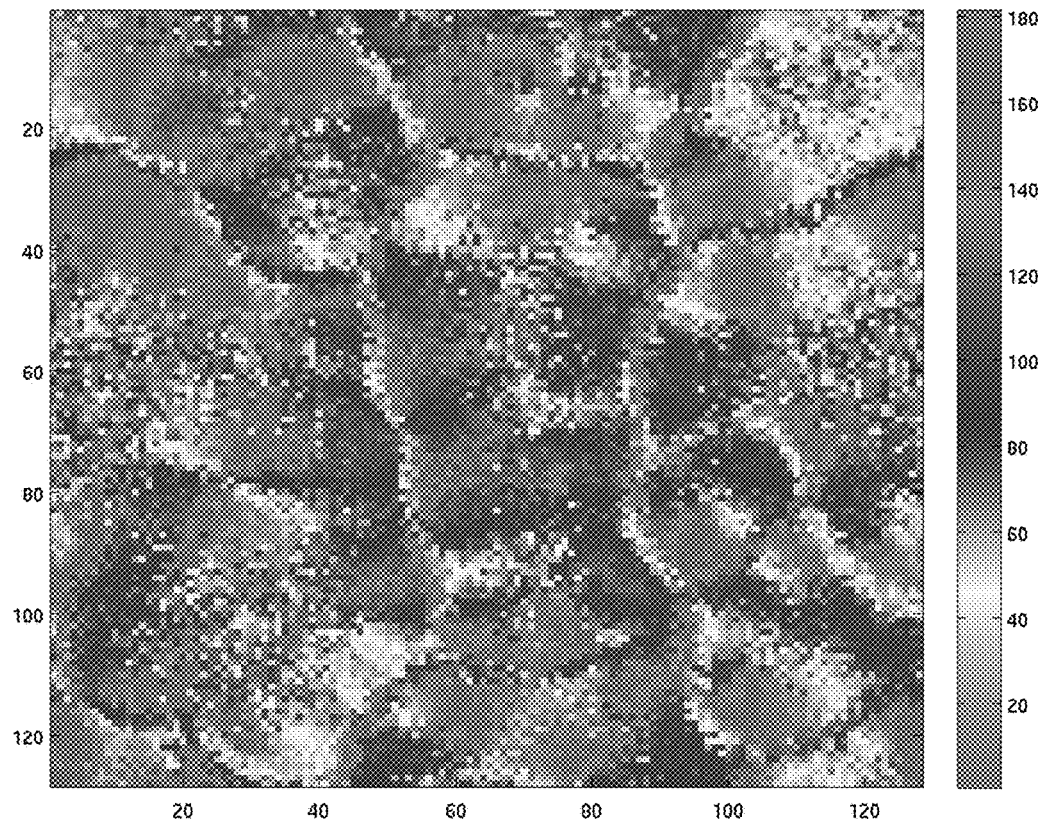
FIGS. 8a-c depict orientation maps in accordance with some embodiments.
Figure 8B:
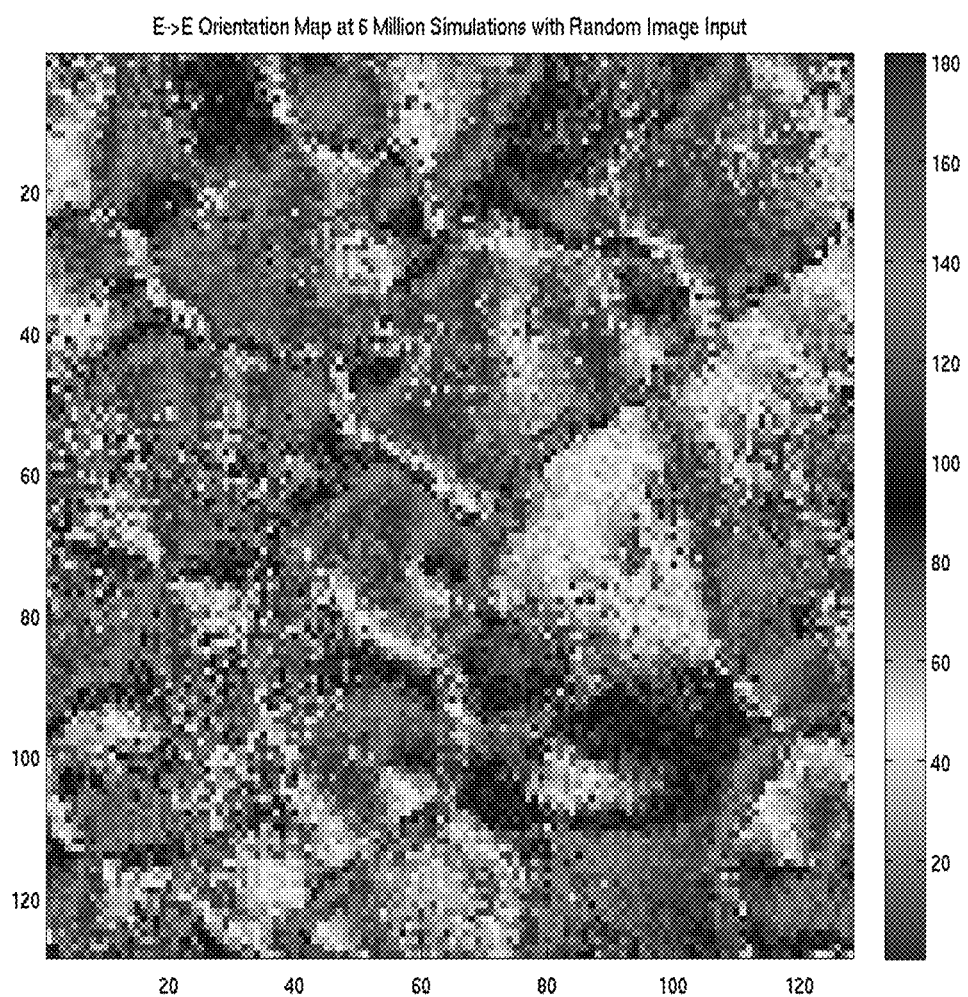

In another exemplary embodiment, the computational model 100 may generate an orientation map for all the excitatory neurons based on the colors assigned the orientation mapping stage 112. FIG. 8a represents an exemplary orientation map generated by the computational model 100 based on the Gaussian random image as shown in FIG. 6a. FIG. 8b represents an exemplary orientation map generated by the computational model 100 based on the random images as shown in FIG. 6b.

In any biological neuron systems, random biological signals always exist; in some case random signals (noise) may play a crucial role to obtain system functions. To model this fact, random currents may be used to model noise in the presently disclosed visual cortex model/computational model 100. The random currents may be injected into each excitatory neuron in the neural network and controlled by a pre-defined injection frequency. The values of random currents may be uniformly distributed in a given range.

Figure 8C:
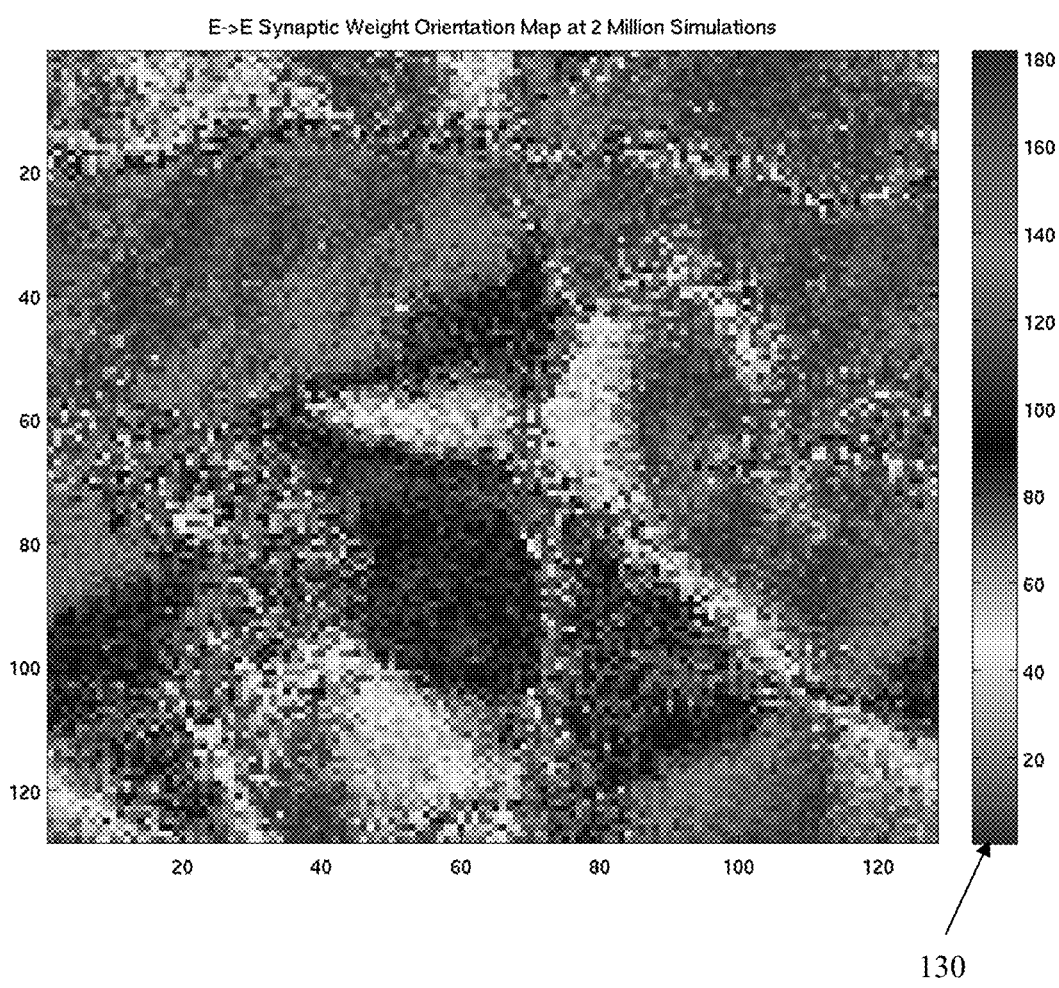

In another exemplary embodiment, the computational model 100 may be configured to generate orientation map without any images from input stage 107. This configuration may be used to simulate a visual cortex of, for example, a baby that has never opened his eyes and has never received any visual external input. FIG. 8c depicts an exemplary orientation map generated by the computational model 100 using only random signals generated by the random signal stage 111. FIG. 8c represents a simulation that ran about 2 million time steps without external stimulus, where each time step is one millisecond. In FIG. 8c, the bar 130 shows the color coded values of orientation degrees; and from the FIG. 8c, it can be seen that the network formed orientation map on visual cortex without any external stimulus, which may be referred to as the self-formation of orientation map.

Contrary to results represented in FIG. 8c, orientation map shown in FIG. 8a was generated using random noise and Gaussian random images shown in FIG. 6a as described above. FIG. 8a represents a simulation that ran first 2 million simulations with random noise from stage 111 and 4 million simulations with Gaussian random images shown in FIG. 6a from stage 107, where each time step is one millisecond. As can be seen, FIG. 8a depicts pinwheel-like patterns that are smaller and sharper than ones in FIG. 8c. Similarly, orientation map shown in FIG. 8b was generated based on a simulation that first ran about 2 million simulations with the random noise from stage 111 and another 4 million simulations with random natural images shown in FIG. 6b from stage 107, where each time step is one millisecond. Similar to FIG. 8a, FIG. 8b depicts pinwheel-like patterns that are smaller and sharper than ones in FIG. 8c. This potentially means that when babies open their eyes, whatever they see will refine the orientation maps on their visual cortex.

The orientation map patterns generated by the presently disclosed computational model 100 were observed in many biological experiments described in an article by T. Bonhoeffer and A. Grinvald, "Iso-orientation domains in cat visual cortex are arranged in pinwheel-like patterns," *Nature,* 353, pp. 429-431, 1991, which is incorporated herein by reference.

Adaptation by Inhibitory Control

Figure 9:
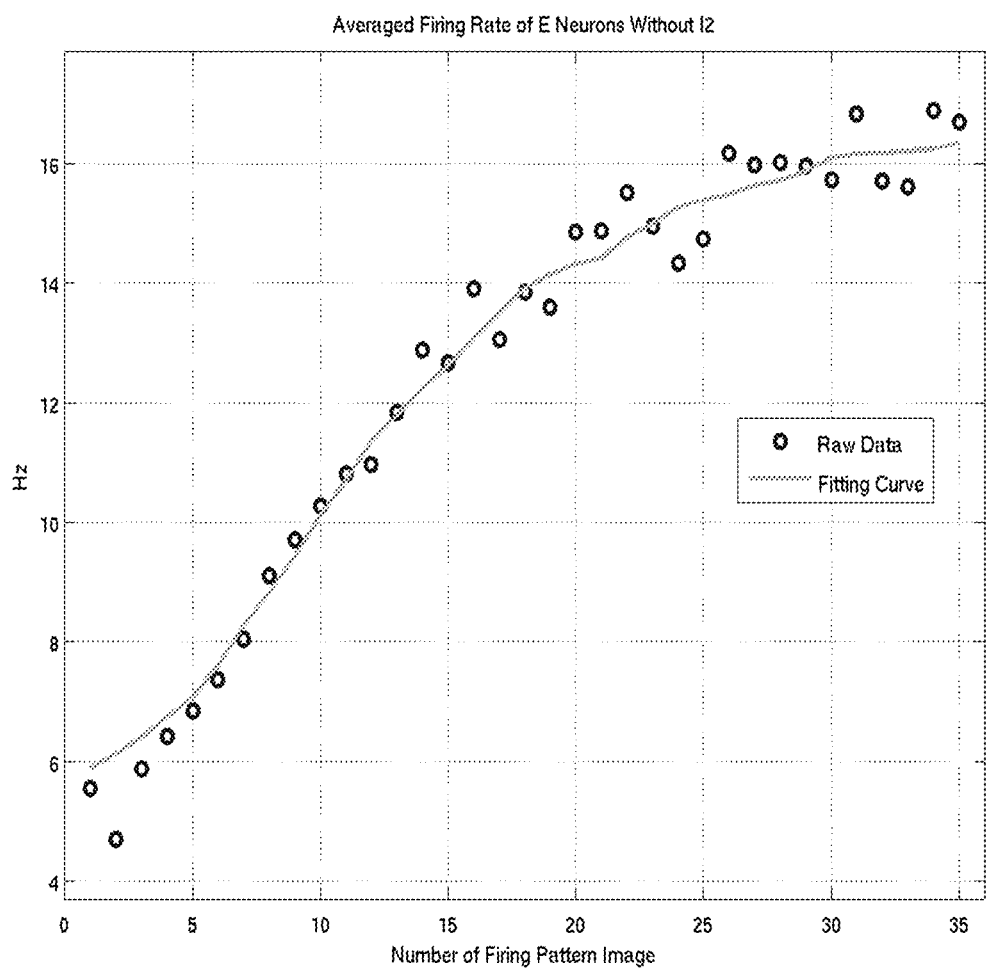
FIGS. 9-10 depict graphs in accordance with some embodiments.
Figure 10:
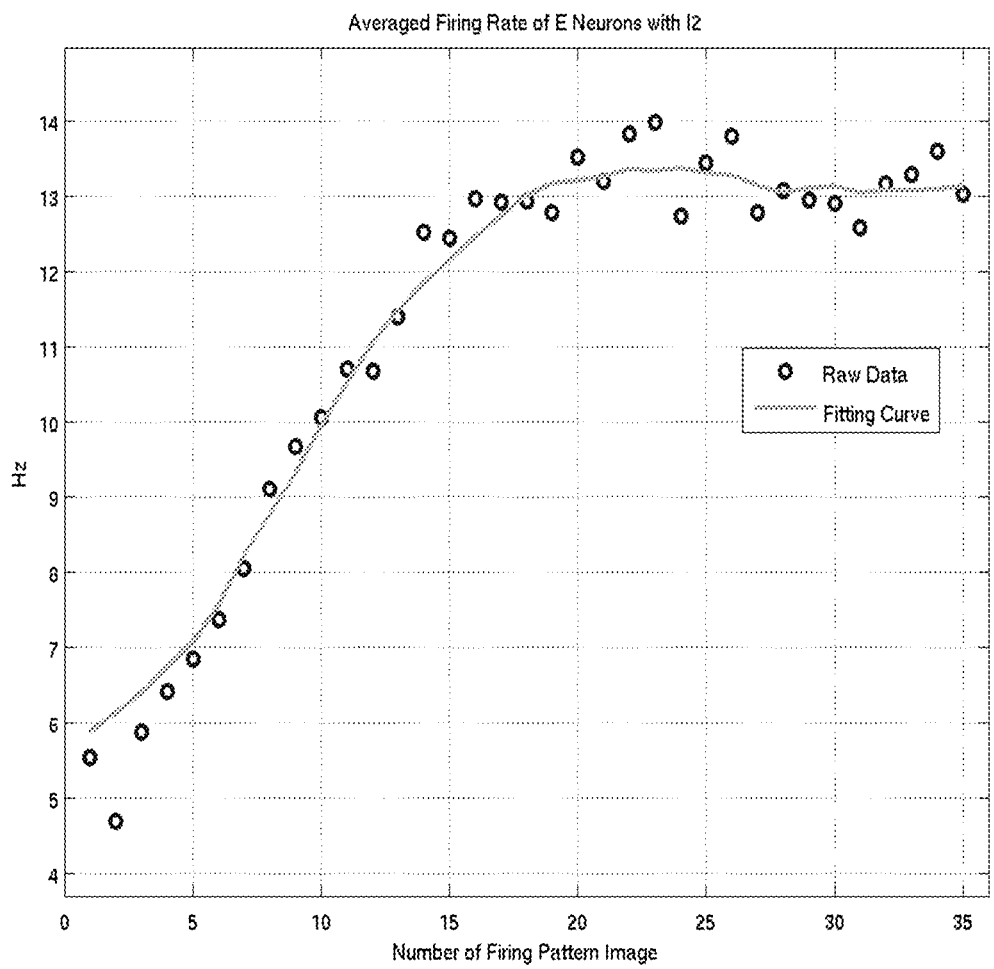
Figure 11A:
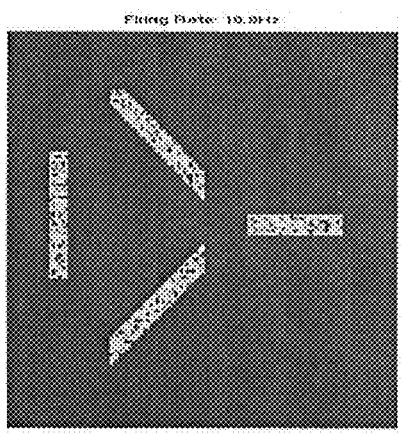
FIGS. 11a-b depict input visual images in accordance with some embodiments.
Figure 11B:
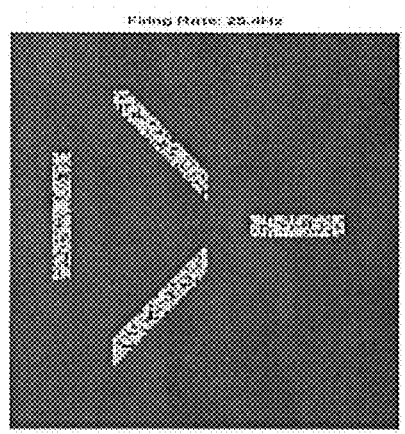

To test the adaptation capability of the computational model 100, 2 million simulations of self-formation phase were run; after the self-formation, another 2 million simulations were run with random Gaussian image shown in FIG. 6a. The inhibitory neurons in neuron layer 20 were able to learn their synaptic weights values through STDP learning in the second 2 million simulations. Then, a simple image with four bars (shown in FIGS. 11a-b) was provided to the computational model 100. The intensity values on the bar images were linearly increased every 2000 simulation time steps. The spiking activities (averaged spiking frequency) on the excitatory neurons were recorded within a 100-time-step window at a 4000 simulation-time-step interval. The spiking activity was recorded for two conditions: one with the inhibitory neuron layer 20 and the other one without the inhibitory neuron layer 20. FIG. 9 depicts the spiking activities for a condition without the inhibitory neuron layer 20. FIG. 10 depicts the spiking activities for a condition with the inhibitory neuron layer 20.

From FIG. 9 and FIG. 10, it can be seen that with the inhibitory neuron layer 20, the spiking activity is stabilized after certain times (20×4000 time steps) while without the inhibitory neuron layer 20, the spiking activity keeps increasing as the intensity values of input image increase. This demonstrates that the computational model 100 of visual cortex has the capability of adaptation to lighting condition changes.

In an exemplary embodiment, the computational model 100 may be implemented using STDP as learning rule for learning synaptic weights. Since STDP can be efficiently implemented by hardware, the computational model 100 may be implemented with hardware and may be scaled up to simulate millions of neurons. As a result, the computational model 100 of visual cortex may be used as a tool/framework to construct more complex neural networks to simulate many high-level visual functions of human visual cortex, such as direction map and objection recognition of the visual cortex. Computational models with high-level visual functions are very useful for developing advanced techniques in computer vision. In addition, the computational model 100 can be used as a research tool for studying human visual cortex in neuroscience as well.

Figure 12:
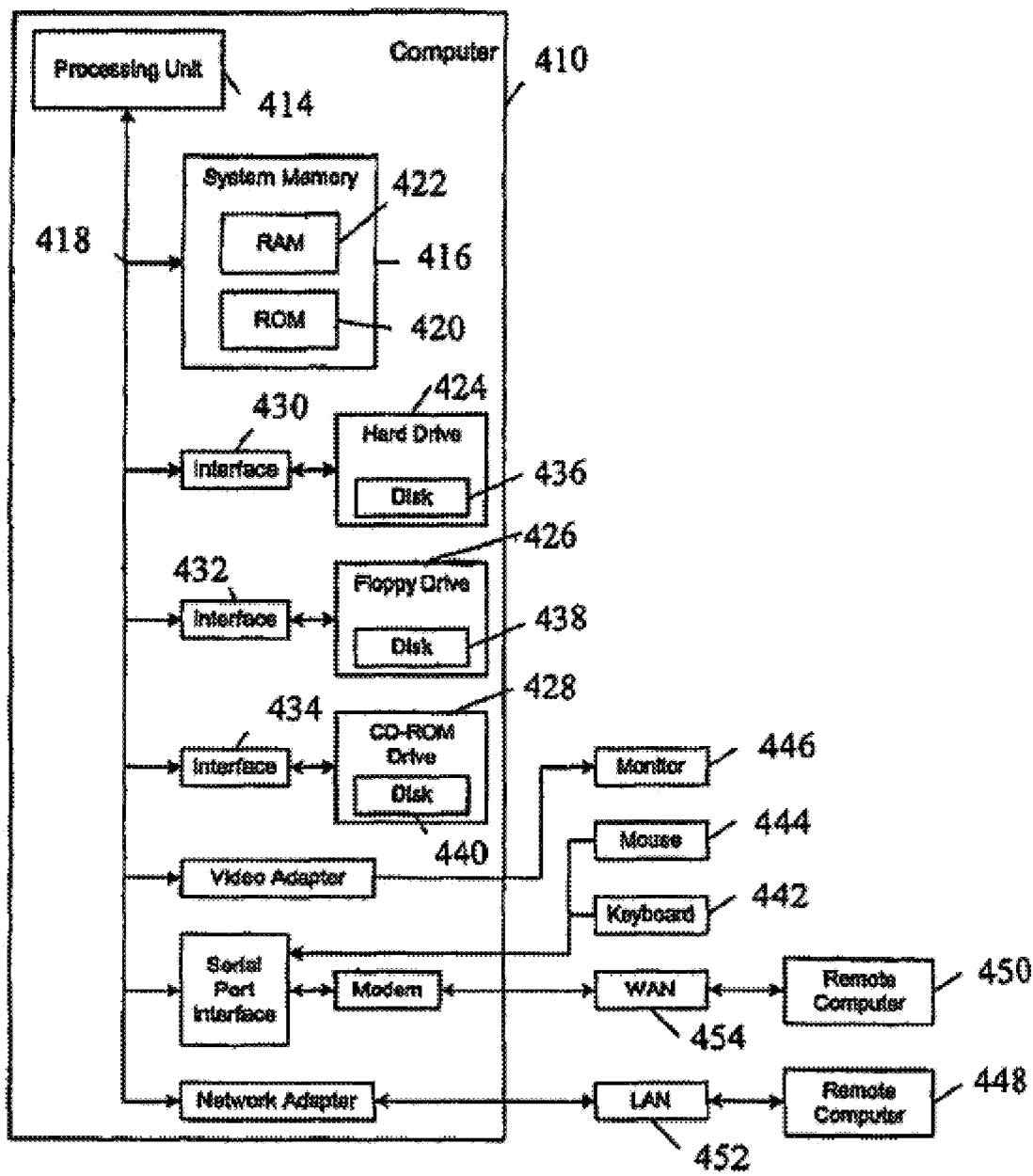
FIG. 12 depicts a computer in accordance with some embodiments.

Referring to FIG. 12, in one exemplary embodiment, the computational model 100 may be implemented as one or more respective software modules operating on a computer 410. Computer 410 includes a processing unit 414, a system memory 416, and a system bus 418 that couples processing unit 414 to the various components of computer 410. Processing unit 414 may include one or more processors, each of which may be in the form of any one of various commercially available processors. System memory 416 includes a read only memory (ROM) 420 that stores a basic input/output system (BIOS) containing start-up routines for computer 410, and a random access memory (RAM) 422. System bus 418 may be a memory bus, a peripheral bus or a local bus, and may be compatible with any of a variety of bus protocols, including PCI, VESA, Microchannel, ISA, and EISA. Computer 410 also includes a hard drive 424, a floppy drive 426, and CD ROM drive 428 that are connected to system bus 418 by respective interfaces 430, 432, 434. Hard drive 424, floppy drive 426, and CD ROM drive 428 contain respective computer-readable media disks 436, 438, 440 that provide non-volatile or persistent storage for data, data structures and computer-executable instructions. Other computer-readable storage devices (e.g., magnetic tape drives, flash memory devices, and digital video disks) also may be used with computer 410. A user may interact (e.g., enter commands or data) with computer 410 using a keyboard 442 and a mouse 444. Other input devices (e.g., a microphone, joystick, or touch pad) also may be provided. Information may be displayed to the user on a monitor 446. Computer 410 also may include peripheral output devices, such as speakers and a printer. One or more remote computers 448 may be connected to computer 410 over a local area network (LAN) 252, and one or more remote computers 450 may be connected to computer 410 over a wide area network (WAN) 454 (e.g., the Internet).

Referring to FIGS. 1a and 2, in one exemplary embodiment, the processing unit 414 is a means for modeling the visual cortex neurons 10, 15, 20 and/or 25; is a means for modeling connection(s) 30 between visual cortex neurons 10, 15, 20 and/or 25; is a means for assigning synaptic weight value 105 to connection(s) 30; is a means for simulating application of one or more electrical signals 106 to the visual cortex neuron(s) 10, 15, 20 and/or 25; is a means for adjusting synaptic weight value assigned to the connection(s) 30 based on the electrical signals; is a means for generating an orientation map 112 of the visual cortex neurons based on the adjusted synaptic weight values While several illustrative embodiments of the invention have been shown and described, numerous variations and alternative embodiments will occur to those skilled in the art. Such variations and alternative embodiments are contemplated, and can be made without departing from the scope of the invention as defined in the appended claims.

As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The foregoing detailed description of exemplary and preferred embodiments is presented for purposes of illustration and disclosure in accordance with the requirements of the law. It is not intended to be exhaustive nor to limit the invention to the precise form(s) described, but only to enable others skilled in the art to understand how the invention may be suited for a particular use or implementation. The possibility of modifications and variations will be apparent to practitioners skilled in the art. No limitation is intended by the description of exemplary embodiments which may have included tolerances, feature dimensions, specific operating conditions, engineering specifications, or the like, and which may vary between implementations or with changes to the state of the art, and no limitation should be implied therefrom. Applicant has made this disclosure with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "step(s) for . . . ."

What is claimed is:

1. A method comprising:
   modeling a plurality of visual cortex neurons comprising:
      a plurality of excitatory neurons in an excitatory neuron layer;
      a plurality of first inhibitory neurons in a first inhibitory neuron layer;
      a plurality of second inhibitory neurons in a second inhibitory neuron layer; and
      a plurality of lateral geniculate nucleus (LGN) neurons in a LGN neuron layer;
   modeling one or more connections between at least two visual cortex neurons in the plurality of visual cortex neurons;
   assigning synaptic weight value to at least one of the one or more connections;
   simulating application of one or more electrical signals to at least one visual cortex neuron in the plurality of visual cortex neurons, the one or more electrical signals comprising a plurality of spiking signals;
   adjusting the synaptic weight value assigned to at least one of the one or more connections based on spiking times of a pre-synaptic spike $t_{pre}$ and a post-synaptic spike $t_{post}$ of the plurality of spiking signals of the one or more electrical signals including increasing the synaptic weight value when $t_{pre}-t_{post}<0$ and decreasing the synaptic weight value when $t_{pre}-t_{post}\geq 0$; and
   generating an orientation map of the plurality of visual cortex neurons based on the adjusted synaptic weight values of connections between the plurality of visual cortex neurons comprising one or more of the excitatory neurons of the excitatory neuron layer, one or more of the first inhibitory neurons of the first inhibitory neuron layer, one or more of the second inhibitory neurons of the second inhibitory neuron layer, and one or more of the LGN neurons of the LGN neuron layer.

2. The method of claim 1, further comprising applying a spiking sequence to at least one visual cortex neuron in the plurality of visual cortex neurons, wherein the spiking sequence is based on noisy electrical signals.

3. The method of claim 2, wherein adjusting the synaptic weight value is based on the spiking sequence applied to the at least one visual cortex neurons of the plurality of visual cortex neurons.

4. The method of claim 1, wherein assigning synaptic weight value to at least one of the one or more connections comprises applying spike timing-dependent plasticity.

5. The method of claim 1, wherein adjusting the synaptic weight value assigned to at least one of the one or more connections based on the one or more electrical signals comprises applying spike timing-dependent plasticity.

6. The method of claim 1, wherein modeling the plurality of visual cortex neurons comprises modeling plurality of lateral geniculate nucleus neurons to receive a spiking sequence, wherein the spike sequence is based on at least a portion of an image.

7. The method of claim 1, wherein generating the orientation map of the plurality of visual cortex neurons based on the adjusted synaptic weight values comprises:
   selecting one visual cortex neuron of the plurality of visual cortex neurons;
   associating one or more visual cortex neurons of the plurality of visual cortex neurons with the selected one visual cortex neuron;
   computing correlation between a Gaussian distribution bar and synaptic weight value associated each of the one or more visual cortex neurons; and
   calculating orientation of synaptic weight value associated each of the one or more visual cortex neurons.

8. The method of claim 1, wherein one or more connections between any pair of neurons are organized using a Gaussian distribution function.

9. The method of claim 1, wherein modeling the plurality of visual cortex neurons comprises implementing a leaky integrate-and-fire model.

10. A computer system, comprising:
    a non-transient memory to store computer-readable code; and
    a processor operatively coupled to said memory and configured to implement said computer-readable code, said computer-readable code configured to:
       model a plurality of visual cortex neurons comprising:
          a plurality of excitatory neurons in an excitatory neuron layer;
          a plurality of first inhibitory neurons in a first inhibitory neuron layer;
          a plurality of second inhibitory neurons in a second inhibitory neuron layer; and
          a plurality of lateral geniculate nucleus (LGN) neurons in a LGN neuron layer;

model one or more connections between at least two visual cortex neurons in the plurality of visual cortex neurons;

assign synaptic weight value to at least one of the one or more connections;

simulate application of one or more electrical signals to at least one visual cortex neuron in the plurality of visual cortex neurons, the one or more electrical signals comprising a plurality of spiking signals;

adjust the synaptic weight value assigned to at least one of the one or more connections based on spiking times of a pre-synaptic spike $t_{pre}$ and a post-synaptic spike $t_{post}$ of the plurality of spiking signals of the one or more electrical signals including increasing the synaptic weight value when $t_{pre}-t_{post}<0$ and decreasing the synaptic weight value when $t_{pre}-t_{post}\geq 0$; and generate an orientation map of the plurality of visual cortex neurons based on the adjusted synaptic weight values of connections between the plurality of visual cortex neurons comprising one or more of the excitatory neurons of the excitatory neuron layer, one or more of the first inhibitory neurons of the first inhibitory neuron layer, one or more of the second inhibitory neurons of the second inhibitory neuron layer, and one or more of the LGN neurons of the LGN neuron layer.

11. A system comprising:
means for modeling a plurality of visual cortex neurons comprising:
a plurality of excitatory neurons in an excitatory neuron layer;
a plurality of first inhibitory neurons in a first inhibitory neuron layer;
a plurality of second inhibitory neurons in a second inhibitory neuron layer; and
a plurality of lateral geniculate nucleus (LGN) neurons in a LGN neuron layer;
means for modeling one or more connections between at least two visual cortex neurons in the plurality of visual cortex neurons;
means for assigning synaptic weight value to at least one of the one or more connections;
means for simulating application of one or more electrical signals to at least one visual cortex neuron in the plurality of visual cortex neurons, the one or more electrical signals comprising a plurality of spiking signals;
means for adjusting the synaptic weight value assigned to at least one of the one or more connections based on spiking times of a pre-synaptic spike $t_{pre}$ and a post-synaptic spike $t_{post}$ of the plurality of spiking signals of the one or more electrical signals including increasing the synaptic weight value when $t_{pre}-t_{post}<0$ and decreasing the synaptic weight value when $t_{pre}-t_{post}\geq 0$; and
means for generating an orientation map of the plurality of visual cortex neurons based on the adjusted synaptic weight values of connections between the plurality of visual cortex neurons comprising one or more of the excitatory neurons of the excitatory neuron layer, one or more of the first inhibitory neurons of the first inhibitory neuron layer, one or more of the second inhibitory neurons of the second inhibitory neuron layer, and one or more of the LGN neurons of the LGN neuron layer.

12. The system of claim 11, further comprising means for applying a spiking sequence to at least one visual cortex neuron in the plurality of visual cortex neurons, wherein the spiking sequence is based on noisy electrical signals.

13. The system of claim 11, further comprising:
means for selecting one visual cortex neuron of the plurality of visual cortex neurons;
means for associating one or more visual cortex neurons of the plurality of visual cortex neurons with the selected one visual cortex neuron;
means for computing correlation between a Gaussian distribution bar and synaptic weight value associated each of the one or more visual cortex neurons; and
means for calculating orientation of synaptic weight value associated each of the one or more visual cortex neurons.

14. The method of claim 2, further comprises
storing the adjusted synaptic weight value, and
storing the spiking sequence.

15. The method of claim 14, further comprises computing statistical patterns based on the stored spiking sequence.

16. The method of claim 1, wherein the synaptic weight value is adjusted based the spiking times of the plurality of spiking signals of the one or more electrical signals in accordance with spike timing-dependent plasticity.

17. The method of claim 1, wherein the one or more connections comprise:
a plurality of first synaptic connections from the LGN neuron layer to the excitatory neuron layer;
a plurality of second synaptic connections from the LGN neuron layer to the first inhibitory neuron layer;
a plurality of third synaptic connections from the first inhibitory neuron layer to the excitatory neuron layer;
a plurality of fourth synaptic connections from the excitatory neuron layer to the second inhibitory neuron layer;
a plurality of fifth synaptic connections from the second inhibitory neuron layer to the second inhibitory neuron layer;
a plurality of sixth synaptic connections from the second inhibitory neuron layer to the excitatory neuron layer; and
a plurality of seventh synaptic connections from the excitatory neuron layer to the excitatory neuron layer.

18. The computer system of claim 10, wherein the one or more connections comprise:
a plurality of first synaptic connections from the LGN neuron layer to the excitatory neuron layer;
a plurality of second synaptic connections from the LGN neuron layer to the first inhibitory neuron layer;
a plurality of third synaptic connections from the first inhibitory neuron layer to the excitatory neuron layer;
a plurality of fourth synaptic connections from the excitatory neuron layer to the second inhibitory neuron layer;
a plurality of fifth synaptic connections from the second inhibitory neuron layer to the second inhibitory neuron layer;
a plurality of sixth synaptic connections from the second inhibitory neuron layer to the excitatory neuron layer; and
a plurality of seventh synaptic connections from the excitatory neuron layer to the excitatory neuron layer.

19. The system of claim 11, wherein the one or more connections comprise:
a plurality of first synaptic connections from the LGN neuron layer to the excitatory neuron layer;

a plurality of second synaptic connections from the LGN neuron layer to the first inhibitory neuron layer;

a plurality of third synaptic connections from the first inhibitory neuron layer to the excitatory neuron layer;

a plurality of fourth synaptic connections from the excitatory neuron layer to the second inhibitory neuron layer;

a plurality of fifth synaptic connections from the second inhibitory neuron layer to the second inhibitory neuron layer;

a plurality of sixth synaptic connections from the second inhibitory neuron layer to the excitatory neuron layer; and a plurality of seventh synaptic connections from the excitatory neuron layer to the excitatory neuron layer.

* * * * *